US010261067B2

(12) United States Patent
Knickerbocker et al.

(10) Patent No.: US 10,261,067 B2
(45) Date of Patent: Apr. 16, 2019

(54) METHOD OF FORMING A FIELD EFFECT BASED NANOPORE DEVICE

(71) Applicant: International Business Machines Corporation, Armonk, NY (US)

(72) Inventors: John U. Knickerbocker, Yorktown Heights, NY (US); Effendi Leobandung, Stormville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/854,994

(22) Filed: Dec. 27, 2017

(65) Prior Publication Data

US 2018/0120288 A1 May 3, 2018

Related U.S. Application Data

(62) Division of application No. 14/694,316, filed on Apr. 23, 2015, now Pat. No. 9,945,836.

(51) Int. Cl.
*G01N 33/487* (2006.01)
(52) U.S. Cl.
CPC .............................. *G01N 33/48721* (2013.01)
(58) Field of Classification Search
CPC ............ H01L 29/786; H01L 29/66477; G01N 33/4872
See application file for complete search history.

(56) References Cited

U.S. PATENT DOCUMENTS 8,093,628 B2 1/2012 Yang et al.
8,558,326 B2 10/2013 Harrer et al.
(Continued)

FOREIGN PATENT DOCUMENTS

CN 103424457 A 12/2013
JP 2013-148425 A 8/2013

OTHER PUBLICATIONS

Yanagi I. et al., "A Novel Side-Gated Ultrathin-Channel Nanopore FET (SGNAFET) Sensor for Direct DNA Sequencing", Electron Devices Meeting (IEDM), IEEE International, pp. 14.3.1-14.3.4 (2013).

(Continued)

*Primary Examiner* — Phuc Dang
(74) *Attorney, Agent, or Firm* — Scully, Scott, Murphy & Presser, P.C.; L. Jeffrey Kelly, Esq.

(57) ABSTRACT

A nanopore FET sensor device and method of making. The nanopore FET sensor device includes a FET device stack of material layers including a source, channel and drain layers, and a nanoscale hole through the FET device stack to permit flow of strands of molecular material, e.g., DNA, therethrough. The perimeter of the nanoscale hole forms a FET device gate surface. The source and drain layers are provided with respective contacts for connection with measuring instruments that measure a flow of current therebetween. The molecular strands having charged portions pass from one side of a wafer substrate to the other side through the (nanopore) gate and modulate the current flow sensed at the source or drain terminals. The sensor collects real-time measurements of the current flow modulations for use in identifying the type of molecule. Multiple measurements by the same nanopore FET sensor are collected and compared for enhanced detection.

12 Claims, 11 Drawing Sheets

(56) References Cited

U.S. PATENT DOCUMENTS

| | | |
|---|---|---|
| 8,618,581 B2 | 12/2013 | Peng et al. |
| 8,698,481 B2 | 4/2014 | Lieber et al. |
| 8,828,138 B2 | 9/2014 | Bedell et al. |
| 2011/0279125 A1* | 11/2011 | Bedell .................... B82Y 15/00 324/444 |
| 2014/0141521 A1 | 5/2014 | Peng et al. |
| 2014/0194298 A1 | 7/2014 | Rothberg et al. |
| 2014/0243214 A1 | 8/2014 | Haga et al. |

OTHER PUBLICATIONS

List of IBM Patents or Patent Applications Treated as Related.
U.S. Appl. No. 15/854,994, filed Dec. 27, 2017, 2018-0120288.

* cited by examiner

METHOD OF FORMING A FIELD EFFECT BASED NANOPORE DEVICE

CROSS-REFERENCE TO RELATED APPLICATIONS

This application is a divisional application of U.S. application Ser. No. 14/694,316, filed Apr. 23, 2015 U.S. Pat. No. 9,945,836 which is incorporated in its entirety herein by this reference.

BACKGROUND

The present disclosure generally relates to nanopore devices, such as used for measuring molecular material such as DNA or chemicals, and particularly to a novel field effect based nanopore device for detecting such materials.

Many macromolecules including deoxyribonucleic acid (DNA) have a shape of a linear chain where each Nucleid (AGTC) carries a different electrical charge. For example, a DNA deoxynucleotide carries an electrical charge that is unique for each base and its ability to change a MOSFET threshold voltage has been documented. An ability of a nano-channel to uncoil DNA and translocate DNA has also been demonstrated in the art.

In particular, FIG. 1 illustrates a prior art field effect based sensor device 5 in which a strand of DNA material 9 including combinations of base nucleotide materials (i.e., A (adenine), G (guanine), C (cytosine) and T (thymine) materials) each having unique charges 6 that act as a gate of a conventional planar FET sensor 5 having a planar source 7 and planar drain 8 electrode structures defining a channel there between. In such structures, the chemical nucleotide materials 9 to be sensed act as a gate, and in a detection system, are caused to pass parallel to the wafer substrate above a gate dielectric 11 (e.g., a high-k layer) for sensing action whereby a conduction between the two drain and gate electrodes passing through the chemical is detected.

Many pairs of nucleotides can be detected at once with trade off accuracy and speed, for example, with a combination of 4 nucleotides, there are about 125 possible base nucleotide material combinations in a typical DNA strand rendering just as many distinct voltage or current levels to detect in a FET sensor. FIG. 2 shows a plot 100 of example combinations of DNA base nucleotide materials and their I-V (current to voltage) characteristic as detected by a FET based sensor, and in particular, based on a detected Vt shift of the nucleotide combination.

While a nanopore sensor has been proposed in silicon compound membranes, e.g., silicon nitride, i.e., where a nanopore is a nanoscale sized hole that may, for example, be created by a pore-forming protein or as a hole in synthetic materials such as silicon or grapheme, by basing conduction between the two electrodes passing through the chemical, the measurements have been difficult to detect.

SUMMARY

A field effect nanopore sensor device and method of its operation to detect molecular items such as DNA where each nucleid (AGTC) carries different charge is disclosed.

The FET nanopore sensor and detection scheme includes combining an ultra small transistor having a gate surface in a nanopore or orifice, and employs threshold voltage shift to detect numerous combination of DNA strand base sequences.

Thus, in one aspect, there is provided a nanopore transistor device. The nanopore transistor device comprising: a substrate; a source terminal layer of a first semiconductor material doped according to a first conductivity type; a channel region of semiconductor material formed atop the source terminal layer, the channel region semiconductor material being doped according to a second conductivity type; a drain terminal layer of semiconductor material formed atop the channel and doped according to the first conductivity type, the drain terminal, channel region and soured terminal layers forming an field effect transistor (FET) device stack; a nanoscale pore (nanopore) formed within FET device stack dimensioned to permit a flow of a molecular material there through, a perimeter of the pore forming a gate surface of the FET device, wherein the molecular material includes portions which contain an electrical charge such that a modulation of current flow between the drain and source is induced as charged portions of the molecular material pass through the pore.

Further to this aspect, the substrate comprises an opening defining a first space in alignment with said FET device stack, said space in fluid communication with said pore; and further comprises: a stack of dielectric material layers formed atop the buried dielectric material layer, said FET device stack being embedded within said dielectric material layers stack, and an opening in said stack of dielectric material layers defines a second space in alignment with said FET device stack, said formed nanopore within said FET device stack in fluid communication with said second space, thereby permitting said flow of a molecular material from said first to said second space.

According to a further aspect, there is provided a method of forming a nanopore transistor device. The method comprises: providing a semiconductor substrate including a buried dielectric material layer; depositing on the semiconductor substrate successive layers of semiconductor material forming an FET device stack, the FET device stack comprising a source terminal layer of a first semiconductor material doped according to a first conductivity type; a channel region of semiconductor material formed atop the source terminal layer and being doped according to a second conductivity type; and a drain terminal layer of semiconductor material formed atop the channel and doped according to the first conductivity type; forming a dielectric material isolation structure above the substrate within which the FET device stack is embedded; etching an opening in the formed dielectric material isolation structure above the substrate to define a first space in alignment with the FET device stack, a surface of the FET device stack exposed within the opening; etching, at the exposed surface, a nanoscale pore (nanopore) within FET device stack dimensioned to permit a flow of a molecular material there through, a perimeter of the pore forming a gate surface of the FET device; and back-etching an opening in the substrate to define a second space in alignment with the FET device stack, the nanopore of the FET device stack in fluid communication with the first and second defined spaces, wherein the molecular material includes portions which contain an electrical charge, such a modulation of current flow between the drain and source is induced as charged portions of the molecular material pass through the pore.

According to yet another aspect of the present disclosure, a method of operating the nanopore FET sensor device described above is provided.

DETAILED DESCRIPTION

Figure 1:
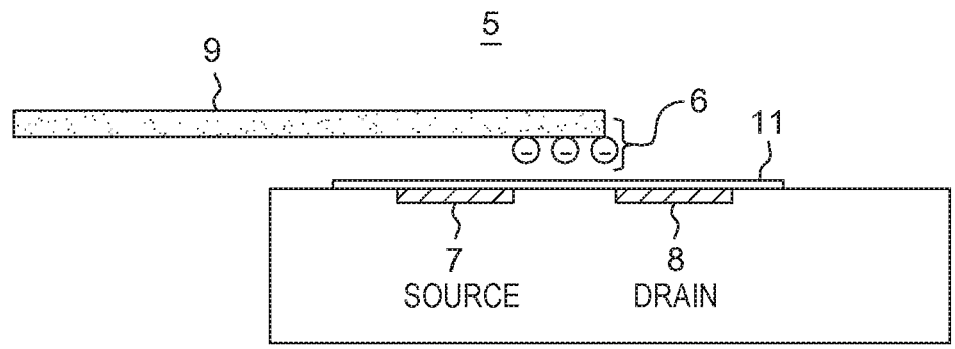
FIG. 1 is a vertical cross-sectional view of a conventional field effect sensing device.
Figure 2:
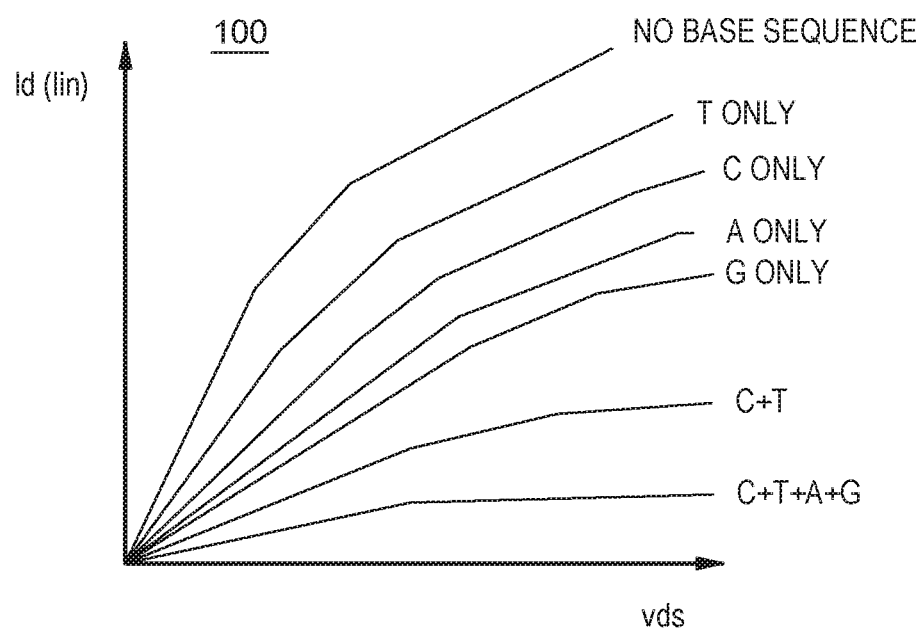
FIG. 2 depict current-voltage response curves for the various combinations of DNA nuclides.

The present disclosure relates to a field effect nanopore device and a method of operation to detect chemical or molecular materials such as DNA, present in a liquid medium such as water. Aspects of the present disclosure are now described in detail with accompanying figures. It is noted that like reference numerals refer to like elements across different embodiments. The drawings are not necessarily drawn to scale. As used herein, ordinals such as "first," "second," and "third," etc. are employed to distinguish similar elements, and a same element may be labeled with different ordinals across the specification and the claims.

Figure 3:
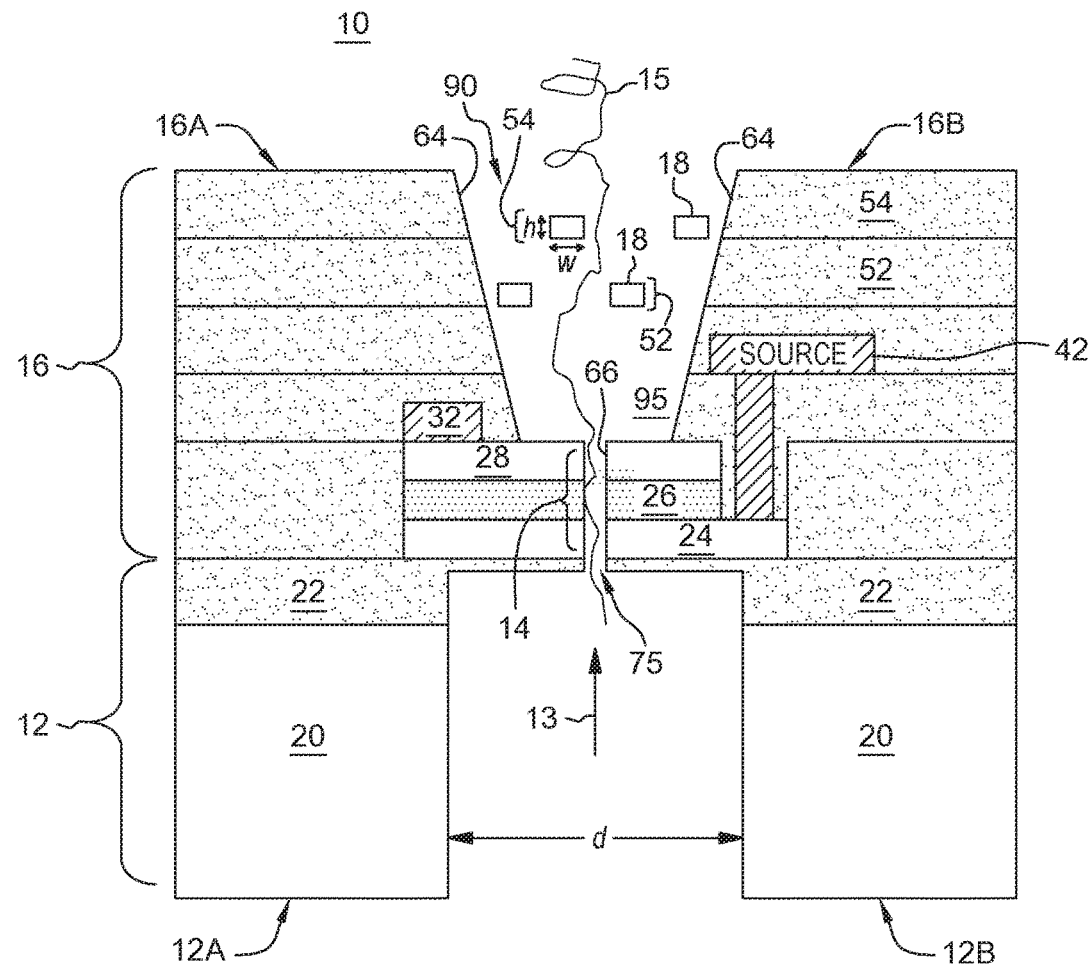
FIG. 3 is a vertical cross-sectional view of the exemplary field effect nanopore device structure according to an embodiment of the present disclosure.

Referring initially to FIG. 3 there is depicted a vertical cross-sectional view of the exemplary field effect nanopore device structure 10 according to an embodiment of the present disclosure. The illustrative field effect nanopore sensor device 10 and method of its operation to detect a type of DNA 15 where each nucleotide (AGTC) carrier or carrier combination provides a different charge is disclosed.

In this embodiment, the nanopore device structure 10 includes a field effect transistor 14 having a semiconductor stack including a drain terminal 28, a source terminal 24, which drain and source terminals define a channel 26 therebetween, and a gate terminal that includes the perimeter of the nanoscale "pore" or "orifice" 75 formed through the stack.

Referring to FIG. 3, there is illustrated a structure 10 employed in one embodiment of the present disclosure. The structure 10 includes, from bottom to top: semiconductor substrate 12 which may be a silicon-on-insulator (SOI) structure including a base substrate 20 and a buried oxide 22 layer. The SOI substrate 12 is shown having portions 12A and 12B separated by opening portion or "space" 13 having of a first diameter d. BOX layers 22 form a base structure upon which are grown a stack 16 of dielectric layers within which a nanopore device 14 of the present invention is located. Located atop each BOX layer 22 of each substrate portion 12A, 12B is a vertical stack of insulating dielectric layers 16. Dielectric layers stack 16 include dielectric layer stack portions 16A, 16B formed above portions of each respective BOX layer 22 of the respective substrate portions 12A, 12B.

Embedded within the dielectric layers stack 16 and formed directly above the space 13 is a stack of layers forming the nanopore FET device 14. In one non-limiting embodiment, the nanopore device 14 includes a formed first layer of semiconductor material, e.g., having a first semiconductor material type, forming a source terminal layer 24, a FET device channel layer 26 formed above the source terminal layer 24, e.g. of a second semiconductor material type, and a formed semiconductor material layer, e.g., of the first semiconductor material type, forming the drain terminal 28, e.g., having the first semiconductor material type, of the nanopore FET device.

Formed at the surface and extending downward within the dielectric layers stack 16 is an opening or aperture 90 defining a space 95 providing a receptacle for receiving and guiding strands of DNA, e.g., in a liquid carrier or like medium as known in the art such as water solution. The opening 90 defines inner sidewall surfaces of each dielectric stack layered portions 16A, 16B. In one embodiment, as shown in FIG. 3, the opening 90 that is etched is configured to form a tapered (or funnel-shaped) sidewall edge, e.g., defining a funnel shaped space 95 at the bottom of which is the nanopore device 14. It is understood that the degree of "taperedness" of the sidewall edge angle with respect to the top surface of the device layer 14 defined by the etching of hole 90 in dielectric stack is configurable. In one embodiment, the inner sidewall edges of respective are defined by straight vertical cuts, resulting in a "cup" non-funnel shape space 95.

Formed in the nanopore FET device 14 is the nanoscale "pore" or "orifice" (nanopore) 75 in fluid communication with both the space 95 defined by the opening 90 and the defined opening portion 13 underneath. This pore 75 is an opening of dimensions sufficient to permit DNA strands to pass through in a liquid medium from the receptacle space 95 defined by opening 90 to the space 13 defined underneath.

In one embodiment, there is formed a thin layer 64 of a high-k gate dielectric material conforming to the inner sidewall surfaces of respective dielectric stack portions 16A, 16B, and atop the surface of the nanopore FET device portion 14, as defined by the formed opening 90. Further, the high-k gate dielectric material layer 66 is extended to conform to and completely line the inner surfaces of the formed pore 75 of device 14.

In an embodiment, the FET device 14 gate terminal includes a DNA strand that includes a charged nucleotide portion that electrically couples with the dielectric gate surface 66 within the "nanopore" 75.

Formed within one of the dielectric layered stack portions, e.g., dielectric stack portion 16A, is a conductive electrode 32 (e.g., a metal contact) contacting the formed drain terminal 28 of the nanopore FET device 14; and formed in the dielectric layered dielectric stack portion 16B is a formed conductive electrode 42 (e.g., a metal contact) contacting the formed source terminal 24 of the nanopore FET device 14. Although not shown, it is understood that further conductors, e.g., conductive lead wires (not shown), may be formed in further back end of line processing to electrically connect the sensor 10, and particularly, electrically connect both the drain 32 and source 42 electrodes of the nanopore FET sensor 10 to an external current or voltage sources and/or external current or voltage measurement device. That is, although not shown, the drain, source are further connected to additional conductive materials in layers (not shown) for routing various current and voltage signal to and from the sensor device 10.

In one embodiment, formed within the space 95 defined by the etched opening 90 and inner surfaces of respective dielectric stack portions 16A, 16B located over the surface of the nanopore FET device channel portion 14 are layers, e.g., layers 52, 54 of spaced apart dielectric rods 18. In one embodiment, in each layer the series of rods lay parallel to the plane defined by the surface of the nanopore FET device channel portion 14. In the embodiment shown in FIG. 3, each rod 18 extends in a transverse orientation, i.e., transverse to a plane defined by the cross-sectional view, and is shown having a height (h) and width (w) dimension. In a further embodiment, the rods 18 within each layer are laterally separated apart by a distance. In a further embodiment, each of the spaced apart rods is configured in a staggered orientation such that the rods 18 in each successive layer 52, 54 do not overlap. That is, given a spaced apart configuration of the extended rods 18 formed in layer 52, a rod formed in layer 54 is located to extend within a space defined above any two adjacent rods extending in the immediately underlying layer, e.g., a space formed in layer 52.

It should be understood that the number, configuration and orientation of the layers of rods 18 extending within space 95 as described herein or shown in the figures is not limiting. That is, further embodiments may alter one or more of: the number of layers of rods, the number of rods within a layer, the physical dimensions (e.g., height and width) of the rods, the lateral spacing between the rods in each layer, the orientation of the rods with respect to rods in adjacent layers, and the overall configuration of the space 95 defined by the sidewall surfaces of the hole 90 located over the surface of the nanopore FET device 14. In each embodiment, the number of layers, the number of rods within each layer, the physical dimensions (e.g., height and width) of the rods, the lateral spacing between the rods in each layer, the orientation of the rods with respect to rods in adjacent layers, and/or the overall "taperedness" configuration of the rods extending within the space 95 is such that they perform a function of straightening or "uncoiling" DNA strands present via a solution within the space, such as shown as strand 15. The number of layers of rods, the number of rods within each layer, the physical dimensions (e.g., height and width) of the rods, the lateral spacing between the rods in each layer, the orientation of the rods with respect to rods in adjacent layers, and/or the overall taperedness or configuration of the rods extending within the space 95 is such that they perform a further function to funnel the uncoiled DNA strands in orientation optimized for real-time detection at the nanopore FET gate surface within orifice 75, and specifically optimized for detection and/or measurement of current-voltage properties of the strand when touching or coupled to the nanopore FET gate surface 66 along the length of the FET layers 24-28.

As MOSFET current flow depends on bias at the gate, operation of the nanopore device 10 employs detection of the current between drain and source terminals as caused by different gate bias due to presence of DNA strand. In the nanopore device 10 of FIG. 3, the nanopore FET "gate" is a three-dimensional (3D) nanopore (hole), the gate surface being the perimeter of the formed nanopore hole 75. The DNA strands are caused to flow via a medium from the space 95 through the nanopore 75 and into the space 13. While a single DNA strand moves within the nanopore 75, real-time current changes from the source to drain terminals are detected, and from the detection of real-time current (or voltage) changes, the sequence of the base in the DNA strand are determined. That is, as the gate bias of nanopore FET 10 depends on the combination of charges attached to the gate, at the gate surface, i.e., at the perimeter of the formed nanopore 75, a charge caused by physical touching or coupling of the DNA strand to the gate is induced with respect to source or drain, and source and current is modulated from the source and drain.

Thus, in operation, the nanopore FET device 14 formed having a drain electrode and source electrode as shown, will conduct carriers based on the presence of a DNA nucleotide base carrier material passing through the nanopore gate orifice 75. The voltage or current resulting from detecting DNA base carriers sensed by the gate is measured by an electronic current or voltage metering device (not shown) connecting the drain electrode 32 and/or source electrode 42 of structure 10. That is, although not shown, the drain, source terminals may be further connected to additional conductive materials in layers (not shown) for routing various current and voltage signal to and from the sensor device 10.

FIGS. 4A-4L depict a series of schematic cross-sectional diagrams illustrating the results of progressive stages in fabricating nanopore FET structure 10 of FIG. 3 in one embodiment.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application. For purposes of the description hereinafter, the terms "upper", "lower", "right", "left", "vertical", "horizontal", "top", "bottom", and derivatives thereof shall relate to the disclosed structures and methods, as oriented in the drawing figures.

Figure 4A:
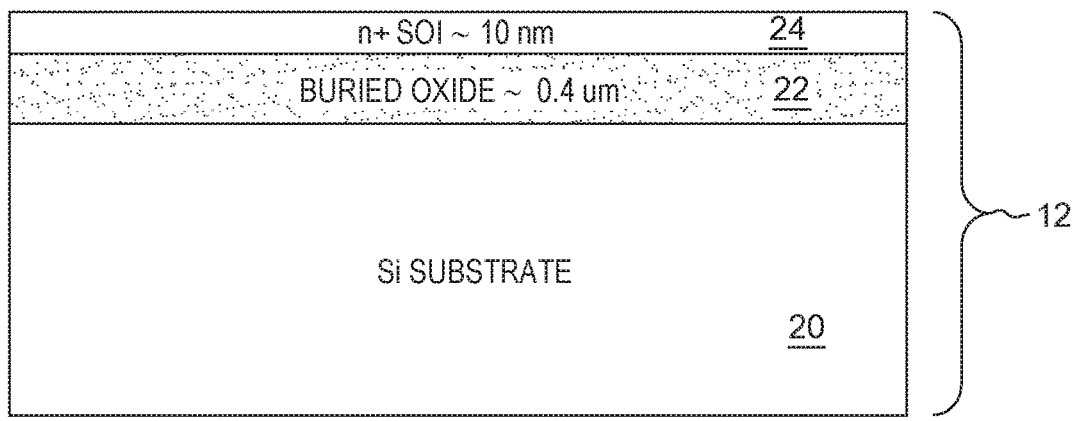
FIG. 4A depicts a vertical cross-sectional view of a structure including an initial semiconductor BOX substrate layer of the device structure of FIG. 3 including a layer forming a first terminal of the nanopore FET device.

FIG. 4A shows the forming of initial semiconductor substrate layer 12 of the structure 10 of FIG. 3.

In one embodiment, the semiconductor substrate 12 can be a bulk single crystalline semiconductor substrate having only a semiconductor material between a planar uppermost surface and a planar bottommost surface. In one embodiment, the semiconductor substrate 20 can include a same single crystalline semiconductor material throughout the entirety thereof.

In the embodiment depicted in FIG. 4A, a semiconductor-on-insulator (SOI) substrate structure is employed as the semiconductor substrate 12. Although not specifically shown, one skilled in the art understands that an SOI substrate includes a handle substrate 20, a buried insulator layer 22 located on an upper surface of the handle substrate 20, and a semiconductor layer 24 located on an upper surface of the buried insulator layer. In one embodiment, the handle substrate provides mechanical support for the buried insulator layer and the semiconductor layers there above.

The handle substrate 20 and the semiconductor layer 24 of the SOI substrate may comprise the same, or different, semiconductor material. The term "semiconductor" as used herein in connection with the semiconductor material of the handle substrate and the semiconductor layer denotes any semiconductor material including, for example, Si, Ge, SiGe, SiC, SiGeC, and III/V compound semiconductors such as, for example, InAs, GaAs, or InP. Multilayers of these semiconductor materials can also be used as the semiconductor material of the handle substrate and the semiconductor layer. In one embodiment, the handle substrate and the semiconductor layer are both comprised of silicon.

In some embodiments, the handle substrate and the semiconductor layer may have the same or different crystal orientation.

The handle substrate and/or the semiconductor layer of the SOI substrate may be a single crystalline semiconductor material, a polycrystalline material, or an amorphous material.

The buried insulator layer 22 of the SOI substrate may be a crystalline or non-crystalline oxide or nitride. In one embodiment, the buried insulator layer is an oxide. Silicon dioxide or silicon oxide are common oxide materials. Other oxide materials are not excluded.

In one embodiment, the buried oxide insulator layer 22 of the SOI substrate may have a thickness from 10 Å to 2000 Å, and in one embodiment, may be about 0.4 micrometers (400 nm) with in thickness. The thickness of the handle substrate of the SOI substrate is inconsequential to the present application.

In one embodiment, the SOI substrate 12 may be formed utilizing standard processes including for example, SIMOX (separation by ion implantation of oxygen), laminating methods or layer transfer processes may be employed. When a layer transfer process is employed, a thinning step may follow the bonding of two semiconductor wafers together.

The optional thinning step reduces the thickness of the semiconductor layer 24 to a layer having a thickness as desired.

In one example, the thickness of the semiconductor layer 24 of the SOI substrate can be from 100 Å (10 nm) or less, for example, if an ETSOI (extremely thin semiconductor-on-insulator) substrate is employed. This layer 24 forms a first terminal of the nanopore FET device, e.g., the source terminal. In one example embodiment, given a P-type channel field-effect nanopore FET, semiconductor layer 24 is subject to further ion implantation, epitaxy an or ion deposition processes to dope the layer 24 with materials of a first conductivity type, e.g., n-type or, specifically, n+-type materials. Exemplary n-type dopants that may be deposited include antimony, arsenic and phosphorous P, As, and Sb. The concentration of dopants forming the n+ type semiconductor material of the semiconductor material layer 24 can range from $1.0 \times 10^{20}/cm^3$ to $1.0 \times 10^{21}/cm^3$, although lesser and greater concentrations can also be employed.

Figure 4B:
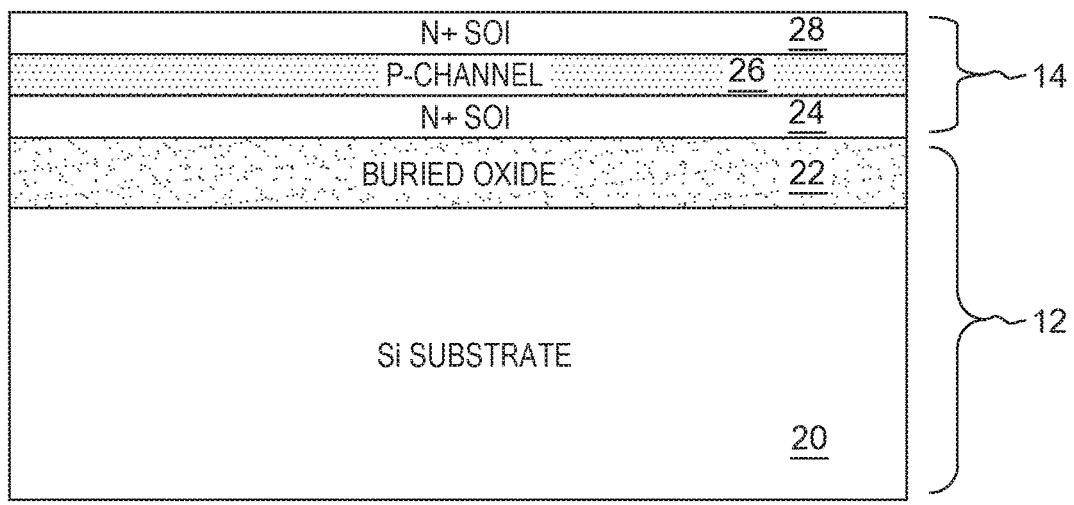
FIG. 4B depicts a vertical cross-sectional view showing the formation of further semiconductor layers including a formed channel of the nanopore FET device, and a second terminal of the nanopore FET device formed atop.

Next, FIG. 4B shows the formation of a semiconductor layer 26 of semiconductor material, of a second conductivity type, e.g., p-type) grown upon the semiconductor layer 24. This layer 26 forms a p-type channel of the nanopore FET device. Semiconductor layer 26 of second conductivity type may be formed utilizing standard epitaxy growth processes, including for example, vapor-phase epitaxy or liquid phase epitaxy, molecular-beam epitaxy.

The epitaxial layer 26 may be doped during deposition with p-type material dopants in a concentration ranging from between $1 \times 10^{17}$ to $1 \times 10^{19}$. Exemplary p-type dopants include boron, aluminum, gallium and indium. In one example, the thickness of the device channel layer 26 of the SOI substrate can range between 2 nm to 10 nm.

It is understood that the terms "epitaxial growing and/or depositing" and "epitaxially formed and/or grown" denote the growth of a semiconductor material on a deposition surface of a semiconductor material, in which the semiconductor material being grown has the same crystalline characteristics as the semiconductor material of the deposition surface. For example, an epitaxial semiconductor material that is formed by an epitaxial deposition process has the same crystalline characteristics as the deposition surface on which it is formed (i.e., an example epitaxial semiconductor material deposited on a {100} crystal surface will take on a {100} orientation). Examples of various epitaxial growth process apparatuses that are suitable for use in the present application include, e.g., rapid thermal chemical vapor deposition (RTCVD), low-energy plasma deposition (LEPD), ultra-high vacuum chemical vapor deposition (UHVCVD), atmospheric pressure chemical vapor deposition (APCVD) and molecular beam epitaxy (MBE).

Thus, in FIG. 4B, the semiconductor layer 26 that is formed as the nFET device body channel region have an epitaxial relationship, i.e., same crystal orientation as the underlying semiconductor layer 24.

FIG. 4B further shows a further formed semiconductor layer 28 of semiconductor material of a second conductivity type, e.g., n_type) grown upon the semiconductor p-type channel layer 26. This semiconductor layer 28 forms a second terminal of the nanopore FET device, e.g., a drain terminal. Semiconductor layer 28 of second conductivity type may be formed utilizing the standard epitaxy growth processes. The epitaxial layer 26 may be doped during deposition with similar n-type material dopants as the source terminal in a concentration same as layer 24. In one example, the thickness of the semiconductor layer 28 forming the drain terminal of the nanopore FET device 14 can be 100 Å (10 nm). As referred to herein, source layer 24, channel layer 26 and drain layer 28 form a stacked FET device layer 14. The concentration of dopants within the source layer 24, channel 26 and the drain layer 28 can be within ranges typically used in forming metal oxide semiconductor field effect transistors (MOSFETs).

Figure 4C:
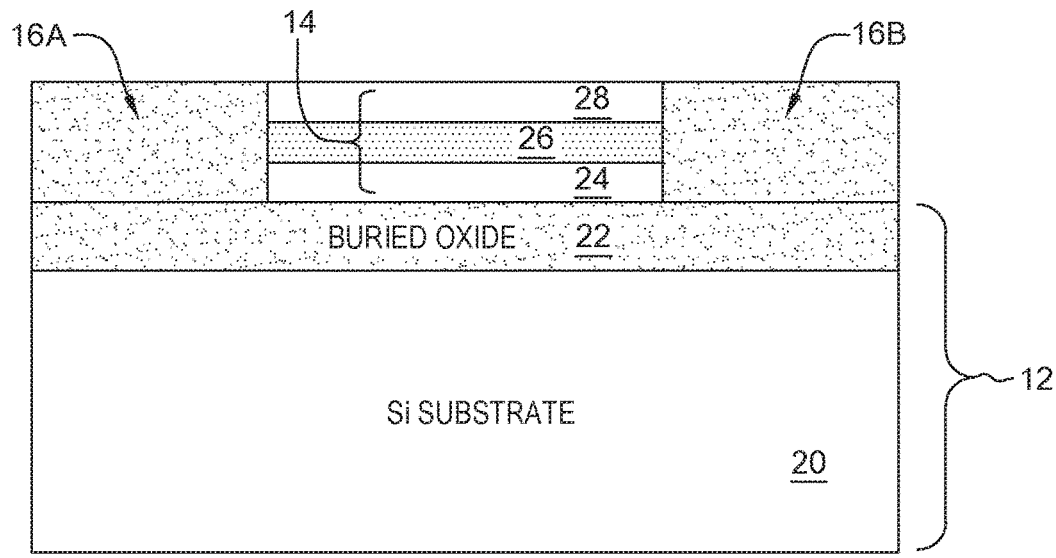
FIG. 4C depicts a vertical cross-sectional view showing a resulting structure after a formation of device isolation regions defining the length of the nanopore FET device.

Next, FIG. 4C shows the formation of a device isolation regions 16A, 16B defining the length of the nanopore FET device channel 26. These isolation regions 16A, 16B may comprises shallow trench isolation structures formed at each end of the stacked FET device layer 14 that contact the underlying buried oxide layer 22 formed by employing methods known in the art. In one embodiment, device isolation layers 16A, 16B formed on either side of device layers 14 employs first forming trenches extending from the top surface of the semiconductor material layer 28 through device layers 14 to the upper surface of the buried oxide layer 22, filling the trenches with a same dielectric material as the underlying buried oxide layer 22, and removing excess dielectric material from above the top surface of the semiconductor material layer 28, e.g., planarizing. The dielectric material may comprise an oxide of silicon, for example.

The dielectric material forming side device isolation regions 16A, 16B can be provided by a deposition process including, for example, chemical vapor deposition (CVD), plasma enhanced chemical vapor deposition (PECVD), or physical vapor deposition (PVD). The etching through the FET device layers 14 material may comprise a dry etch process such as, for example, a reactive ion etch.

Figure 4D:
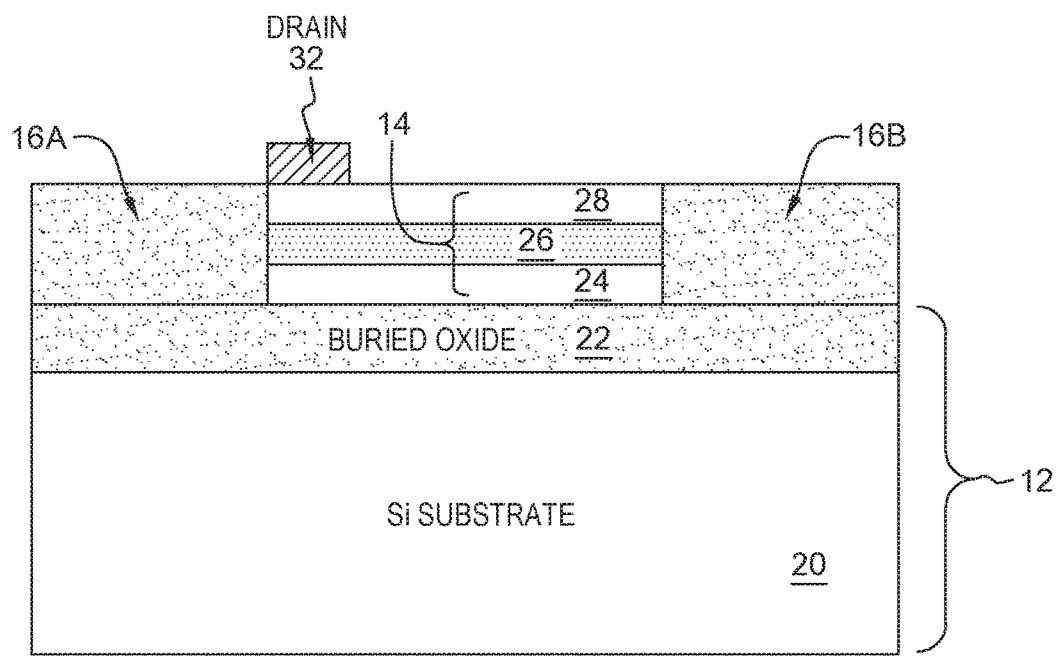
FIG. 4D depicts a vertical cross-sectional view showing a resulting structure after forming a first ohmic metal contact electrode atop of and directly contacting the second terminal of the nanopore FET device.

Next, FIG. 4D shows the deposition of a metal contact electrode 32 atop of and in direct physical contact with the drain terminal (layer 28). Using standard lithographic techniques, such as a lift-off process, as known in the art, the metal contact electrode is formed. For example, such techniques may involve creating an inverse pattern on the underlayer 28. This may entail exposing and developing a photoresist, e.g., according to Extreme ultraviolet lithography—EUVL or Electron beam lithography—EBL. The photoresist is removed in the area where the metal electrode material is to be located (creating an inverse pattern.) Then, standard metal contact deposition techniques, e.g., PVD, sputter deposition, e-beam evaporation, are used to deposit a metal electrode material atop the whole underlying area including the etched region as a thin metal layer (and on the top of the photoresist layer in the remaining un-etched region). This metal layer may be 10-100 nm thick. Then the metal electrode material over the un-etched regions is removed by a chemical solvent, and is lifted-off and removed together with the photoresist layer below. After the lift-off, the metal electrode material remains only in the etched region where it directly contacts underlying transistor terminal, e.g., drain terminal. A metal contact may include a material such as aluminum, gold, copper, nickel, titanium, a metal alloy, or any other metal compound.

Figure 4E:
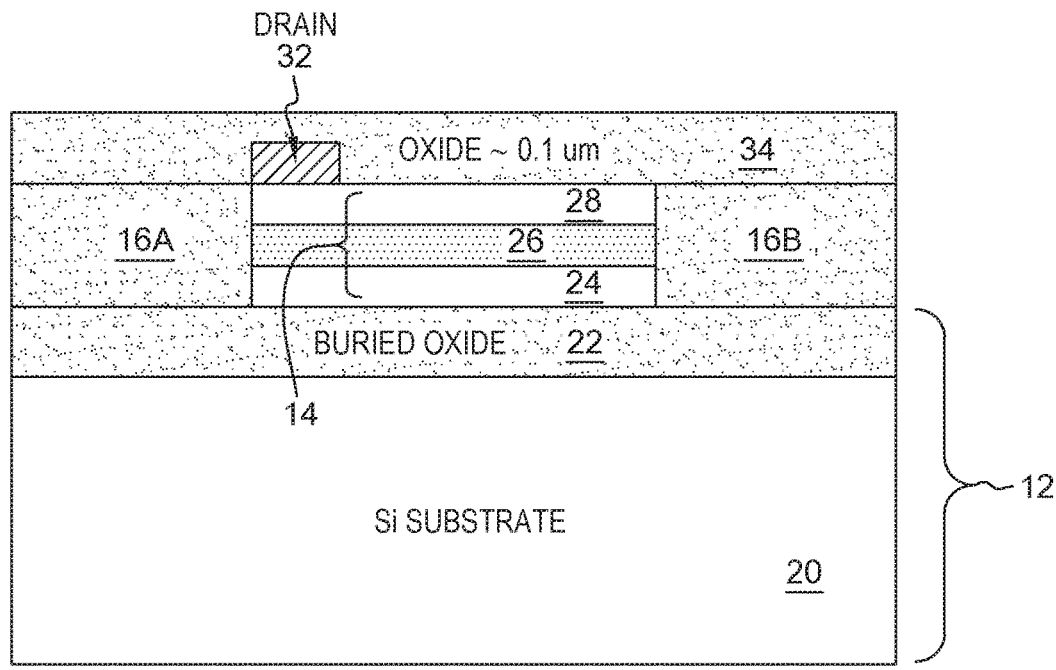
FIG. 4E depicts a vertical cross-sectional view showing a resulting structure after depositing a further dielectric layer atop and covering the metal contact electrode and remaining length of the nanopore FET device and device isolation regions.

Then, in FIG. 4E depicts the deposition of a further dielectric layer 34 atop and covering the metal contact electrode 32, remaining length of the nanopore FET device channel 28, and extending to cover the device isolation regions 16A, 16B. In one embodiment, this layer may include a dielectric, e.g., an oxide of silicon, and is deposited using common thin-film deposition techniques, e.g., CVD. The thickness of the layer material may range between 0.02 and 0.15 micrometers (or wider ranges).

Figure 4F:
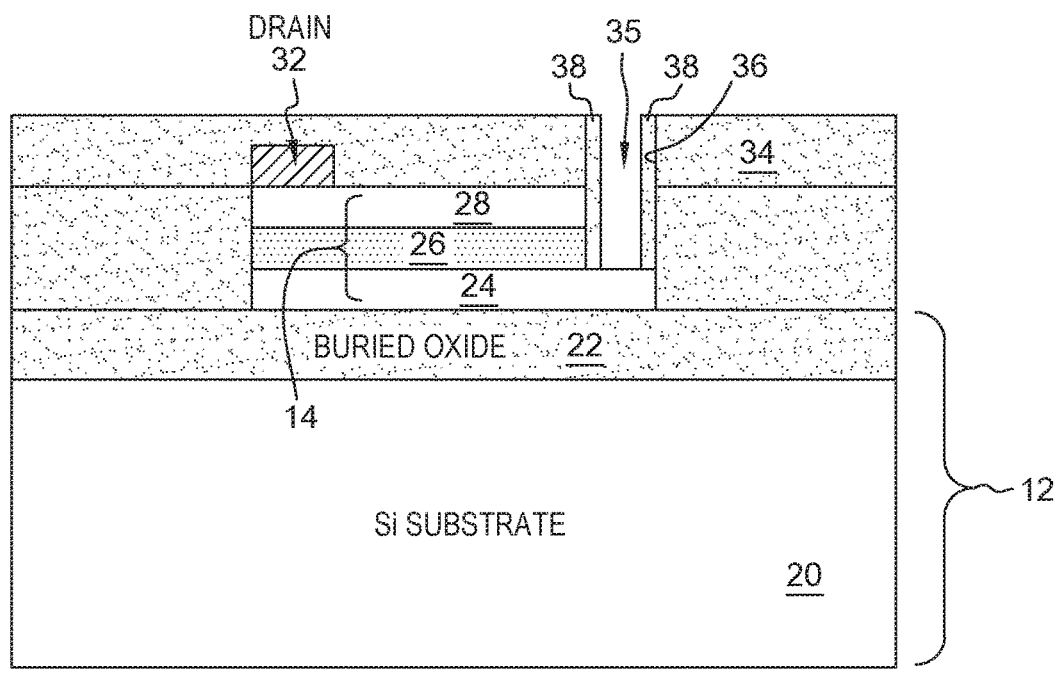
FIG. 4F depicts a vertical cross-sectional view showing a resulting structure after opening of a contact via through the dielectric layer and through the second terminal and channel layers of nanopore FET device layers to a surface of the other terminal of the nanopore FET device.

Next, in the cross-sectional view of FIG. 4F, there is shown the resulting structure after opening of a contact via 35 through the dielectric layer 34 and through device layers 28, 26 to a surface of the other underlying device terminal, i.e., source terminal layer 24 of the FET device. This may include lithographic processes including forming a mask to pattern the hole and etching, such as by using a Reactive Ion Etch (RIE), to open up the via 35. It is noted that the etch employed to remove the dielectric layer and device layers 28 and 26 may be performed by a wet or dry etch that is selective to the semiconductor material of the source layer 24. In the embodiment depicted, the via or hole 35 is opened up such that the source contact to be formed is aligned to the source terminal at a device edge 36 opposite the formed drain contact.

Then using known semiconductor processing techniques, a thin dielectric layer 38 such as an oxide of silicon is coated or otherwise formed only on inner surface sidewalls such that sidewall surfaces of the contact via 35 are insulated, i.e., lined with dielectric material.

Figure 4G:
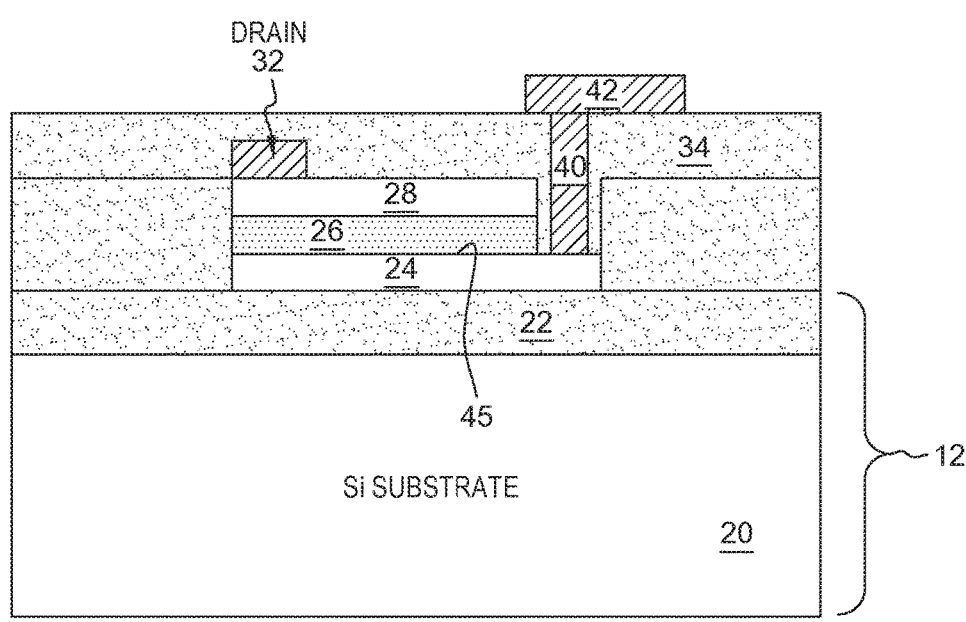
FIG. 4G depicts a vertical cross-sectional view of a resulting structure after forming an second ohmic metal contact electrode to the first terminal layer of the nanopore FET device.

Next, in the cross-sectional view of FIG. 4G there is shown the result of forming an ohmic contact 40 to the source terminal layer 24 by depositing metal material inside the opened via 35 such that the metal contacts the surface 45 of the underlying source layer 24. Example metal materials deposited may include, but are not limited to: aluminum, gold, copper, nickel, titanium, a metal alloy, or any other metal compound, such as by PVD deposition process.

Then, using known lift-off processes such as described herein above for forming drain contact 32, a source metal contact 42 is formed atop dielectric layer 34 only in a region where it directly contacts underlying source contact electrode 40 contacting the underlying FET transistor terminal, e.g., n+ semiconductor material source terminal layer 24.

Figure 4H:
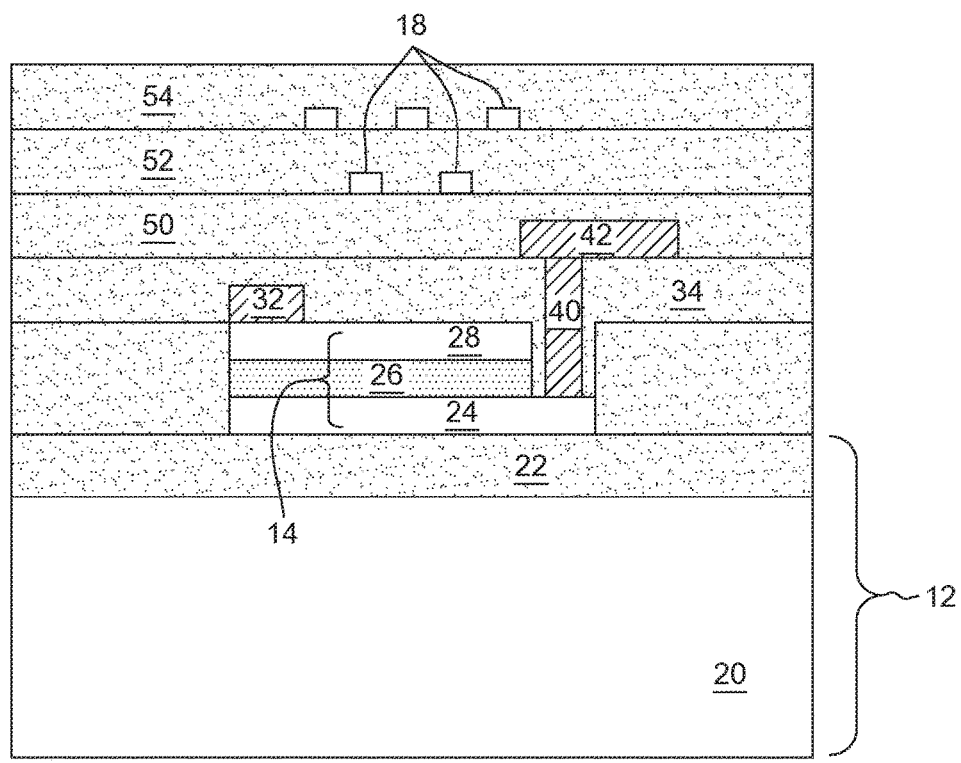
FIG. 4H depicts a vertical cross-sectional view of a resulting structure after depositing further successive layers of dielectric material to embed and cover the second metal contact electrode, and one or more layers including one or more transverse oriented, spaced-apart insulating rod structures.

Next, in the cross-sectional view of FIG. 4H there is shown the resulting structure after depositing further dielectric layer 50 atop layer 34 and covering the metal contact electrode 42, and then planarizing the surface of that layer 50, and also the result of depositing and planarizing of successive dielectric material layers 52 and 54 atop the layer 50. In one embodiment, these layers 52, 54 may comprises a dielectric material, e.g., an oxide of silicon, and are deposited one at a time, using common thin-film deposition techniques, e.g., CVD, PVD or spin coating. The thickness of the dielectric material layer 50 may range between 0.1 and 1 micrometers. As each layer 52, 54 is formed, one or more rod structures 18 are formed spaced apart therein using known photolithographic processes, e.g., pattern etch, deposition, planarizing, etc. For example, a dielectric layer may be deposited and photolithography processes used to apply a mask used to form a trench at one or more spaced apart locations where a rod 18 is to be placed in the layer.

In this process, a trench height "H" and width "W" define the corresponding dimensions of a rod 18. The trenches then are filled with an insulating material, e.g., silicon nitride, or any dielectric that is not an oxide, or other material such as metal that is different than material of layers 50, 52, 54. The distance between any two adjacent rods 18 on a layer may be spaced anywhere from between 100 nm to 10 microns. After forming the rod structure, a dielectric material is further deposited and the surface of the resulting structure is planarized using known processes. Then a further deposition of dielectric material is deposited to completely embed the rod(s) in that layer. The process is repeated for each subsequent layer, e.g., layer 54, formed. This process of depositing dielectric material and rod structures spaced linearly therein may be repeated depending upon the size of the sensor, and may comprise 2-5 layers, or up to 10 layers or more.

In one embodiment, each rod formed is of a dimension of size 0.1 μm by 1 μm in an example embodiment. The rod length can be around 1-10 μm and is such that it extends substantially through the formed opening 90 and is embedded within the dielectric layers at opposing sides of the hole 90. Additionally, in the embodiment, shown, the location of the rod formed in each layer may be staggered with respect to rods formed in the adjacent row above (or below) it. Additionally, the rods 18 are formed in a tapered manner such that row 54 has more insulating rod structures than the underlying row 52, and are spaced further out. As mentioned, the number of layers, the number of rods within each layer, the physical dimensions (e.g., height and width) of the rods, the lateral spacing between the rods in each layer, the orientation of the rods with respect to rods in adjacent layers, and/or the overall "taperedness" configuration of the rods embedded within the layers is configurable to straighten and uncoil the DNA chains.

Figure 4I:
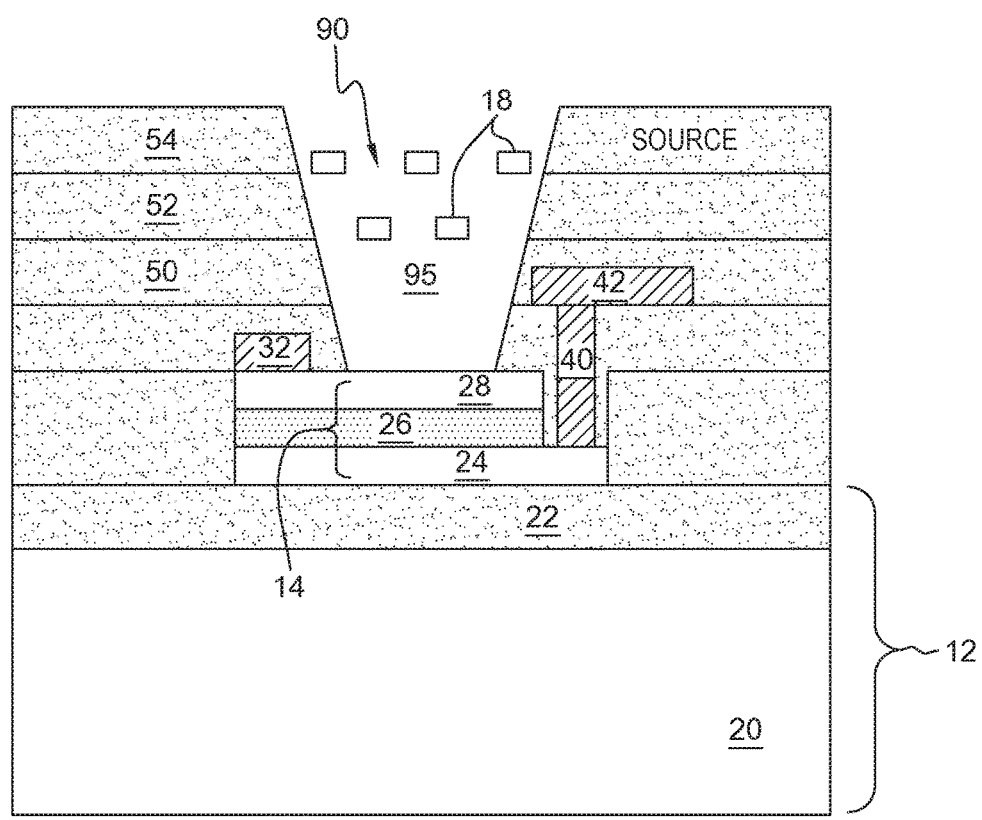
FIG. 4I depicts a vertical cross-sectional view of a resulting structure after performing a tapered-etch selective to the second terminal layer of the nanopore FET device to form a space within which insulating nitride rods remain suspended in transverse orientation.

Then, in the cross-sectional view of FIG. 4I, there is shown the result of a tapered-etch defining an opening 90 to form the space 95. The insulative nitride rods 18 remain suspended in a configuration as described herein and are anchored at opposite ends 19 that remain embedded within the dielectric layers 52-54, as shown in the top view of FIG. 4K. The configuration of suspended nitride rods 18 act as a DNA straightener. The etch is selective to the dielectric materials forming the layers 50, 52 and 54 and do not affect the formed rods 18 within the dielectric stack.

Figure 4J:
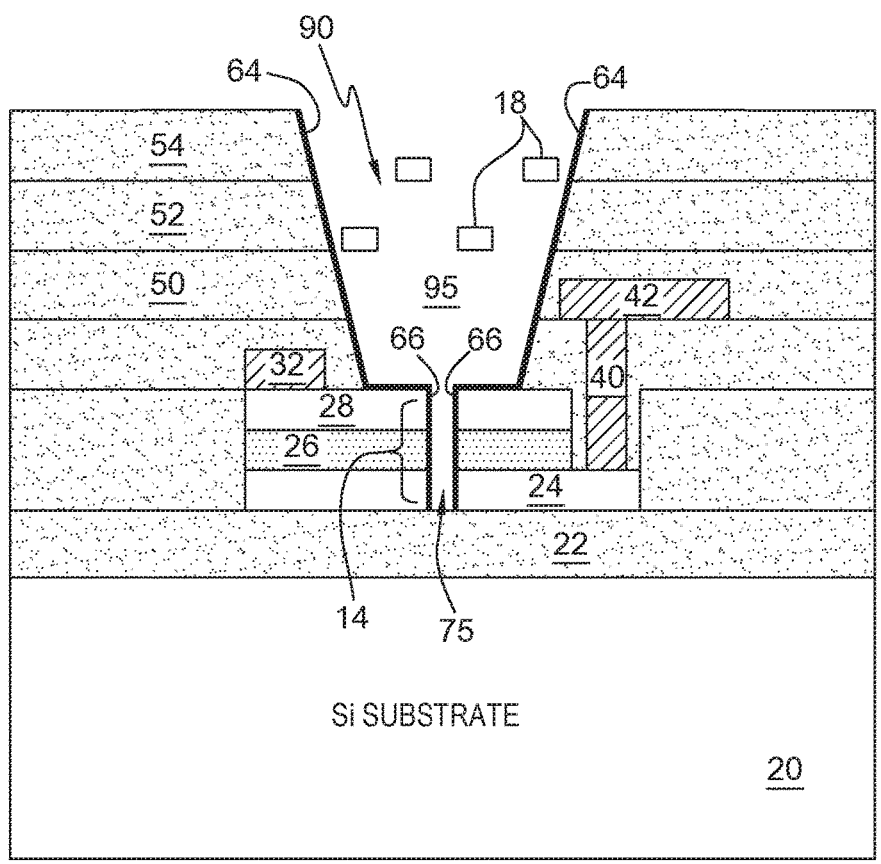
FIG. 4J depicts a vertical cross-sectional view of a resulting structure after performing an etch process to create the nanopore opening extending through each FET device terminal and channel layers and through a portion of the underlying BOX oxide layer, and including the deposition of a high-k gate dielectric lining the interior of formed space, and nanopore opening.
Figure 4K:
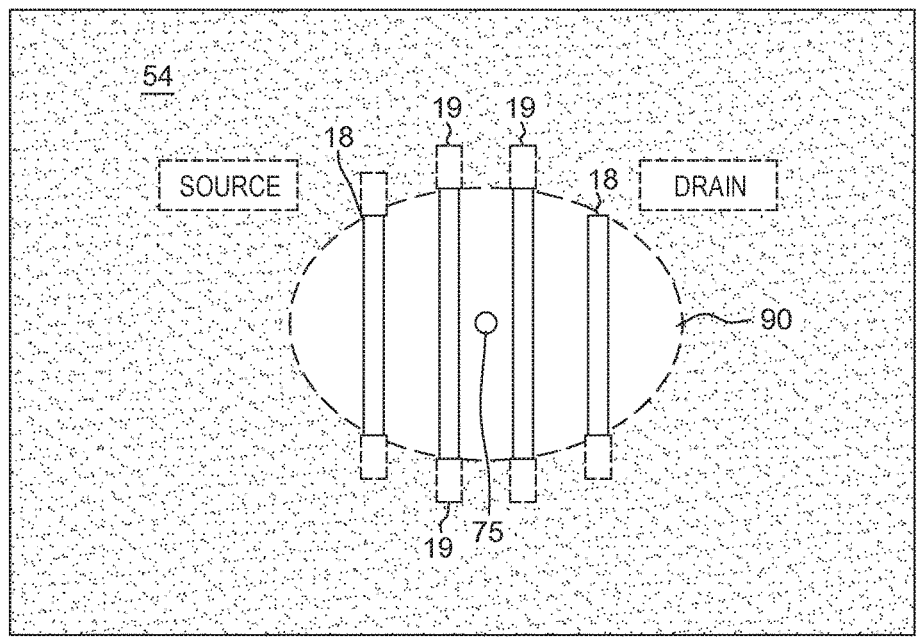
FIG. 4K depicts a top down view of a resulting structure after forming the nanopore opening and showing the configuration of transverse oriented nitride rods for straightening DNA strands to facilitate their movement for detection through said nanopore opening.

Then, in the cross-sectional view of FIG. 4J, there is shown the resulting structure after performing an etch process performed to create the nanopore opening 75 that extends through each FET device layers 24-28 and through a portion of the underlying BOX layer 22. In one embodiment, the formed nanopore opening 75 is a hole approximately 2 nm to 10 nm in diameter, or at least wide enough to permit one molecular strand of DNA to pass through. A plasma etch and/or known anistotropic directional etch process may be employed to generate the nanopore opening 75.

Then, in view of FIG. 4J, a thin conformal gate dielectric layer 64 is deposited on the inside sidewall surfaces of the nanopore hole 75, and deposited as thin layer 64 on all sidewall surfaces of the formed space 95 defined in opening 90.

In one embodiment, the gate dielectric layer 64, 66 can be a semiconductor oxide, a semiconductor nitride, and/or a semiconductor oxynitride. In one example, the gate dielectric material 64, 66 can be composed of silicon dioxide, silicon nitride and/or silicon oxynitride. In another embodiment of the present application, the gate dielectric material 64, 66 may include a high dielectric constant (high-k) material layer having a dielectric constant greater than 8.0. Exemplary high-k materials include, but are not limited to, $HfO_2$, $ZrO_2$, $La_2O_3$, $Al_2O_3$, $TiO_2$, $SrTiO_3$, $LaAlO_3$, $Y_2O_3$, $HfO_xN_y$, $ZrO_xN_y$, $La_2O_xN_y$, $Al_2O_xN_y$, $TiO_xN_y$, $SrTiO_xN_y$, $LaAlO_xN_y$, $Y_2O_xN_y$, SiON, $SiN_x$, a silicate thereof, and an alloy thereof. Each value of x is independently from 0.5 to 3 and each value of y is independently from 0 to 2. In one embodiment, the gate dielectric layer 42L is a hafnium oxide ($HfO_2$) layer. The gate dielectric layers 66, 64 conforming to the surface sidewall in the space 95 and in the nanopore hole 75, respectively, can be formed by a conventional deposition process, including but not limited to, CVD, PVD, ALD, molecular beam epitaxy (MBE), ion beam deposition, electron beam deposition, and laser assisted deposition. The gate dielectric layers that is formed may have a thickness ranging from 0.9 nm to 6 nm with a thickness ranging from 1.0 nm to 3 nm being more typical. The gate dielectric layer 66 may have an effective oxide thickness on the order of or less than 1 nm. Other thicknesses that are lesser than or greater than the aforementioned thickness range can also be employed for the gate dielectric material 64, 66.

Figure 4L:
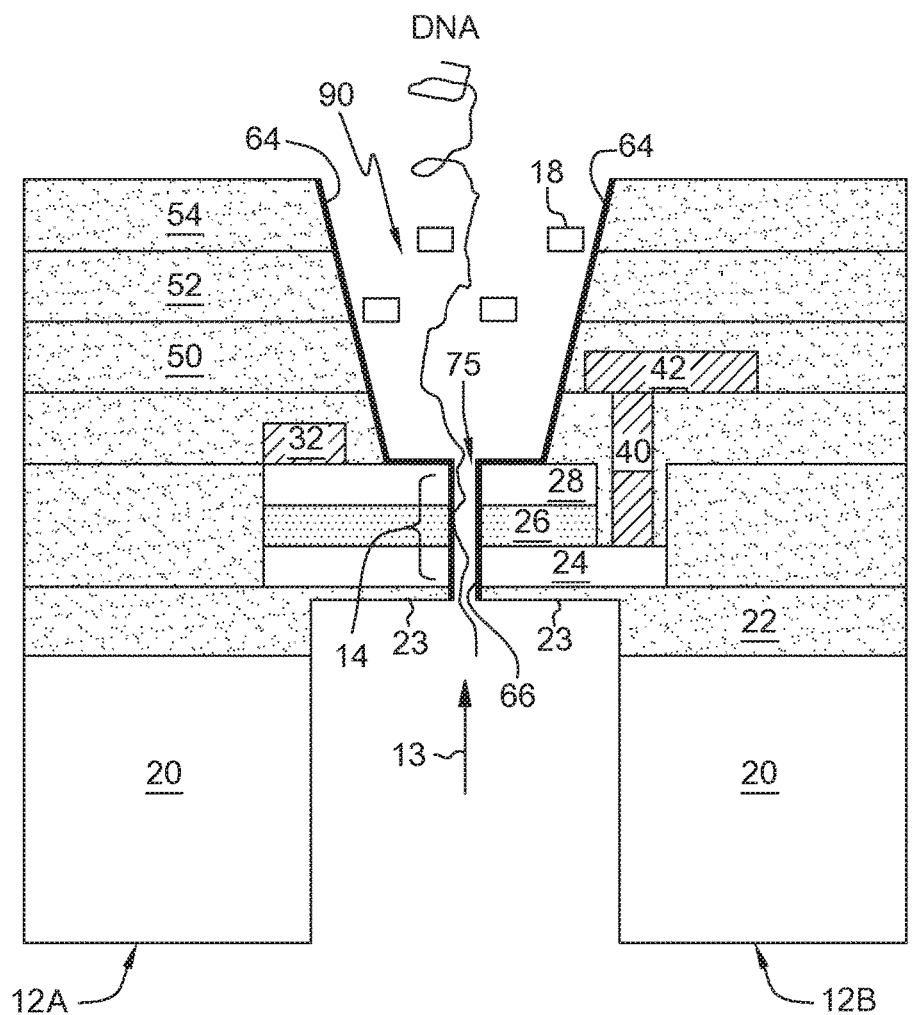
FIG. 4L depicts a vertical cross-sectional view of a resulting structure after performing an etch to remove portions of the substrate and BOX to form a further space defined between substrate portions that is in fluid communication with the nanopore opening.

FIG. 4L shows the resulting structure after a further process is performed to etch portions of the substrate 20 and BOX 22 in the manner as shown that removes all semiconductor substrate material to form the space 13 defined between substrate portions 12A, 12B, which space 13 is in fluid communication with the nanopore opening 75. However, rather than completely etching the underlying BOX layer 22, the hole 75 is extended through at least a thin portion 23 of the underlying BOX layer 22. This thin BOX portion 23 in which nanopore hole 75 extends through may be approximately 10 nm in thickness and can function as a passivation layer 23.

As a result of processing depicted in FIGS. 4A-4L, the resulting sensor device 10 of FIG. 3 is formed within an enclosure that permits the flow of fluid having molecular materials therein. Thus, in operation of the sensor 10, the DNA or molecular strand 15 (or other chemical material) to be sensed in the fluid solution passes from one side of wafer substrate to the other through the nanopore 75. The formed series of spaced apart straightening rods 18 above the nanopore gate 75 function as straighteners for uncoiling strands of DNA and straightening the DNA strands and guiding the straightened DNA strands 15 to pass through the nanopore or orifice gate 75 for sensing thereof by measuring a real-time current or voltage modulation of carriers in the channel (i.e., induced by the linear chain of charged portions of the DNA strand passing through the nanopore 75) between the drain and source terminals. For example, in one embodiment, the nanopore FET sensor 10 employs threshold voltage shift to detect numerous combination of base sequences of the DNA strand. A solution containing DNA can be dropped on top of opening 90 and as the solution migrates through opening 75 (e.g., because of gravity) into defined opening 13, the DNA will also migrate through.

Further devices and structures based on the device of FIG. 3 may be implemented. For example, in a further embodiment, there may be formed a sensor device having multiple nanopore FET transistors, e.g., in a sequence (not shown), with each transistor having its own nanopore opening and separate drain and source terminals connected to corresponding measurement devices. Each of the multiple transistors in a sensor may each connect to an individual measuring devices for better discrimination and error correction of the current and voltage signals detected as a molecular chain, e.g., DNA molecule, passes through an opening of a respective transistor. That is, embodiments include employing many nanopore FET transistor devices, e.g., in a sequence or a series, for obtaining measurements with increased noise reduction and error correction. In such an embodiment, the molecular strands (e.g., of the same DNA material) may pass through each of multiple transistors (pores) and real-time measurement signals obtained from each transistor device may be collected and processed, e.g., compared with each other for error correction.

As a further device and structure based on the device of FIG. 3, in a further embodiment, there may be formed a sensor device having a single transistor with multiple nanopore openings (not shown). Each of the multiple nanopore openings in the nanopore FET sensor may provide redundancy as greater opportunity for detection of DNA strands by the nanopore gate sensing.

As a further device and structure based on the device of FIG. 3, in a further embodiment, there may be formed a sensor device having multiple transistors in series sharing the same nanopore opening. In this embodiment, there may be two or more FET sensor device vertically oriented with respect to each other, and each with its own source and drain contacts as in FIG. 3, however, each device shares the same nanopore opening. Thus, respective source and drain contacts of each of the two or more FET sensor device vertically oriented will be connected to an individual measuring device. Thus, a single molecular strand may pass through three transistors and thus, may have real-time measurements collected at each transistor, which may be processed for error correction purposes.

As a further device and structure based on the device of FIG. 3, in a further embodiment, functionality may be added to the gate insulator by attaching different chemical/enzyme, etc. to the gate insulator layer 66 to enhance detection.

In a further embodiment, the FET nanopore sensor detection scheme may employ many such nanopore transistors in a sequence for enhanced noise reduction and error correction.

While the disclosure has been described in terms of specific embodiments, it is evident in view of the foregoing description that numerous alternatives, modifications and variations will be apparent to those skilled in the art. Each of the various embodiments of the present disclosure can be implemented alone, or in combination with any other embodiments of the present disclosure unless expressly disclosed otherwise or otherwise impossible as would be known to one of ordinary skill in the art. Accordingly, the disclosure is intended to encompass all such alternatives, modifications and variations which fall within the scope and spirit of the disclosure and the following claims.

What is claimed is:

1. A method of forming a nanopore transistor device comprising:
    providing a semiconductor substrate including a buried dielectric material layer;
    depositing on said semiconductor substrate successive layers of semiconductor material forming an FET device stack, said FET device stack comprising a source terminal layer of a first semiconductor material doped according to a first conductivity type; a channel region of semiconductor material formed atop said source terminal layer and being doped according to a second conductivity type; and a drain terminal layer of semiconductor material formed atop said channel and doped according to said first conductivity type;
    forming a dielectric material isolation structure above said substrate within which said FET device stack is embedded;
    etching an opening in said formed dielectric material isolation structure above said substrate to define a first space in alignment with said FET device stack, a surface of said FET device stack exposed within said opening;
    etching, at said exposed surface, a nanoscale pore (nanopore) within FET device stack dimensioned to permit a flow of a molecular material therethrough, a perimeter of said pore forming a gate surface of said FET device; and
    back-etching an opening in said substrate to define a second space in alignment with said FET device stack, said nanopore of said FET device stack in fluid communication with said first and second defined spaces, wherein the molecular material includes portions which contain an electrical charge, such a modulation of current flow between said drain and source is induced as charged portions of said molecular material pass through said pore.

2. The method of claim 1, wherein said substrate further comprises a buried dielectric material layer, said source terminal of said FET device stack formed on a portion of said buried dielectric material layer, said buried dielectric material layer having a surface exposed to said defined second space, wherein said etched nanopore within FET device stack extending through said buried dielectric material layer in fluid communication with said second space.

3. The method of claim 1, wherein said forming a dielectric material isolation structure above said substrate comprises:
    forming a stack of dielectric material layers formed atop the buried dielectric material layer, said FET device stack being embedded within said dielectric material layers stack.

4. The method of claim 3, further comprising:
    forming, in one or more dielectric material layers of said stack, one or more dielectric material rod structures in lateral, spaced-apart relation at one or more levels above said formed nanopore opening, wherein a dielectric material of said rod is different than a dielectric material of said formed said dielectric material layers stack such that said rod structures are not etched during forming said opening to define said first space, and each said formed rod structure embedded at opposing ends that within the dielectric material layers stack.

5. The method of claim 4, further comprising:
    forming said one or more dielectric material rods in a staggered orientation such that rod structures formed in said lateral spaced-apart relation at a first level within said first space are not aligned with a rod structure at a second level within said first space.

6. The method of claim 4, further comprising: coating an inner surface of said nanopore opening and a surface said opening formed in said stack of dielectric material layers defining said first space with a high-k dielectric material layer.

7. The method of claim 4, further comprising:
    forming a first metal electrode in physical contact with said drain terminal layer of said FET device stack and extending from the drain terminal layer within said stack of dielectric material layers; and
    forming a second metal electrode in physical contact with said source terminal layer of said FET device stack and extending from the source terminal layer within said stack of dielectric material layers.

8. A method of operating a nanopore FET sensor device having a substrate, a source terminal layer of a first semiconductor material doped according to a first conductivity type, a channel region of semiconductor material formed atop said source terminal layer, said channel region semiconductor material being doped according to a second conductivity type, a drain terminal layer of semiconductor material formed atop said channel and doped according to said first conductivity type, and wherein said drain terminal, channel region and source terminal layers form an field effect transistor (FET) device stack; and a nanoscale hole (nanopore) formed within FET device stack dimensioned to permit a flow of a molecular material therethrough, a perimeter of said pore forming a gate surface of said FET device, the method comprising:

providing a solution with molecular material, said nanopore FET sensor device in fluid communication with said solution for receiving said molecular material at said nanopore, wherein the molecular material includes portions which contain an electrical charge, inducing a modulation of a current flow between said drain terminal and source terminal, responsive to said portions which contain an electrical charge flowing through said nanopore;

real-time detecting said modulation of current flow between said drain and source terminals, and identifying a type of molecular material based on said detected modulated current flow.

9. The method of claim 8, wherein said nanopore FET sensor device further comprises:

a buried dielectric material layer, said source terminal of said FET device stack formed on a portion of said buried dielectric material layer; and a stack of dielectric material layers formed atop the buried dielectric material layer, said FET device stack being embedded within said dielectric material layers stack; and one or more dielectric material rod structures formed in one or more dielectric material layers of said stack of dielectric material layers, oriented in lateral, spaced-apart relation at one or more levels above an opening of said nanopore, said step of receiving said molecular material at said nanopore further comprising:

straightening, using said dielectric material rod structures, said strands of said molecular material within the solution prior to flow within said nanopore.

10. The method of claim 9, wherein said straightening, using said dielectric material rod structures, said strands of said molecular material, comprises:

uncoiling said strands of said molecular material within the solution using said dielectric material rod structures.

11. The method of claim 8, wherein said nanopore FET sensor device further comprises:

an opening defining a space extending downward within the dielectric layers stack providing a receptacle for receiving said solution, said space in communication with said opening of said nanopore, said step of receiving said molecular material at said nanopore further comprising:

guiding said strands of molecular material in said solution towards said nanopore opening.

12. The method of claim 11, wherein sidewalls defining said space extending downward within the dielectric layers stack are tapered, said step of receiving said molecular material at said nanopore further comprising:

funneling said strands of molecular material in said solution towards said nanopore opening.

* * * * *